US006617142B2

(12) United States Patent
Keogh et al.

(10) Patent No.: US 6,617,142 B2
(45) Date of Patent: *Sep. 9, 2003

(54) METHOD FOR ATTACHMENT OF BIOMOLECULES TO MEDICAL DEVICE SURFACES

(75) Inventors: James R. Keogh, Maplewood, MN (US); Paul V. Trescony, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,543

(22) Filed: Feb. 24, 1999

(65) Prior Publication Data

US 2002/0001834 A1 Jan. 3, 2002

Related U.S. Application Data

(63) Continuation of application No. 09/067,188, filed on Apr. 27, 1998, now Pat. No. 5,925,522, which is a continuation-in-part of application No. 09/001,994, filed on Dec. 31, 1997, now Pat. No. 5,945,319, which is a continuation-in-part of application No. 08/635,187, filed on Apr. 25, 1996, now Pat. No. 5,821,343, application No. 09/257,543, which is a continuation-in-part of application No. 08/984,922, filed on Dec. 4, 1997, now Pat. No. 5,891,506, which is a continuation-in-part of application No. 08/694,535, filed on Aug. 9, 1996, now Pat. No. 5,728,420, application No. 09/257,543, which is a continuation-in-part of application No. 09/012,056, filed on Jan. 22, 1998, now Pat. No. 6,033,719, and a continuation-in-part of application No. 09/010,906, filed on Jan. 22, 1998, now Pat. No. 5,928,916.

(51) Int. Cl.⁷ ........................ C12N 11/00; A61K 38/43; G01N 33/543; C07K 17/00

(52) U.S. Cl. .................... 435/174; 424/178.1; 424/94.1; 435/176; 435/177; 435/180; 435/181; 436/518; 436/524; 436/531; 436/532; 530/402; 530/810; 530/811; 530/812; 530/815; 530/816

(58) Field of Search ................................. 435/174, 176, 435/177, 180, 181; 424/178.1, 94.1; 436/518, 524, 528, 531, 532; 530/402, 810, 811, 812, 815, 816

(56) References Cited

U.S. PATENT DOCUMENTS

| | | | |
|---|---|---|---|
| 3,826,678 A | 7/1974 | Hoffman et al. | 424/420 |
| 4,442,133 A | 4/1984 | Greco et al. | 427/2.25 |
| 5,069,899 A | 12/1991 | Whitbourne et al. | 424/56 |
| 5,344,455 A | 9/1994 | Keogh et al. | 623/11 |
| 5,429,618 A | 7/1995 | Keogh | 604/266 |
| 5,728,420 A | * 3/1998 | Keogh | 427/2.12 |
| 5,821,343 A | * 10/1998 | Keogh | 530/402 |
| 5,891,506 A | * 4/1999 | Keogh | 427/2.13 |
| 5,925,552 A | * 7/1999 | Keogh et al. | 435/174 |
| 5,928,916 A | * 7/1999 | Keogh | 435/174 |
| 5,945,319 A | * 8/1999 | Keogh | 435/174 |
| 6,033,719 A | * 3/2000 | Keogh | 427/2.12 |

OTHER PUBLICATIONS

Hoffman et al., "Covalent Binding of Biomolecules to Radiation–Grafted Hydrogels on Inert Polymer Surfaces," *Trans. Am. Soc. Artif. Intern. Organs*, 18, 10–18 (1972).

Ito et al., "Materials for Enhancing Cell Adhesion by Immobilization of Cell–Adhesive Peptide," *J. Biomed. Mat. Res.*, 25, 1325–1337 (1991).

Gott et al., "Heparin Binding On Colloidal Graphite Surfaces," *Science* 142, 1297–1298 (1963).

Grode et al., "Nonthrombogenic Materials via a Simple Coating Process," *Trans. Amer. Soc. Artif. Intern. Organs*, 15, 1–6 (1969).

Barbucce et al., "Surface–Grafted Heparinizable Materials," *Polymer*, 26, 1349–1352 (1985).

Wirsen et al., "Bioactive heparin surfaces from derivatization of polyacrylamide–grafted LLDPE", *Biomaterials*, 17, 1881–1889 (1996).

Sano et al., "Introduction of functional groups onto the surface of polyethylene for protein immobilization", *Biomaterials*, 14, 817–822 (1993).

(List continued on next page.)

*Primary Examiner*—David M. Naff
(74) *Attorney, Agent, or Firm*—Kenneth Collier; Thomas Woods

(57) ABSTRACT

Methods are provided for forming a coating of an immobilized biomolecule on a surface of a medical device to impart improved biocompatibility for contacting tissue and bodily fluids. A biomolecule such as a glycoprotein having an unsubstituted amide moiety is combined with an amine forming agent to form an amine-functional biomolecule. The amine-functional biomolecule is combined with a medical device surface having a chemical moiety such as aldehyde, epoxide, isocyanate, 1,2-dicarbonyl, phosphate, sulphate or carboxylate to form a chemical bond immobilizing the biomolecule on the surface. The chemical bond may be combined with a reducing agent or a stabilizing agent. The aldehyde moiety may be formed by combining a periodate with a 2-aminoalcohol moiety or a 1,2-dihydroxy moiety. Alternatively, an amine-functional medical device surface is combined with a biomolecule having a chemical moiety that reacts with an amine moiety. In another embodiment, the amine-functional biomolecule is converted to a guanidino-functional biomolecule and is combined with a medical device surface having a chemical moiety that reacts with a guanidino moiety. Alternatively, an amine-functional medical device surface is converted to a guanidino-functional surface and is combined with a biomolecule having the chemical moiety. Biomolecules may be crosslinked by combining the amine-functional or guanidino-functional biomolecule with a biomolecule having a chemical moiety that forms a chemical bond with an amine moiety or a guanidino moiety.

53 Claims, No Drawings

OTHER PUBLICATIONS

Full et al., "A new class of amino acid based sweeteners", *J. Am. Chem. Soc.*, 107, 5821–5822 (1985).

Loudon et al., "Conversion of aliphatic amides into amines with [I,I–bis(trifluoroacetoxy)iodo]benzene. 1. Scope of the reaction", *J. Org. Chem.*, 49, 4272–4276 (1984).

*Comprehensive Organic Synthesis*, vol. 6, 800–806, Pergamon Press.

Kajigaeshi et al., "An efficient method for the Hofmann degradation of amides by use of benzyltrimethylammonium tribromide", *Chemistry Letters*, 463–464 (1989).

Dickinson and Jacobsen, *Chem. Commun.*, 1719 (1970).

O'Farrell, "High Resolution Two–dimensional Electrophoresis of Proteins", *J. Biol. Chem.* 250, 4007–4021 (1974).

* cited by examiner

METHOD FOR ATTACHMENT OF BIOMOLECULES TO MEDICAL DEVICE SURFACES

CROSS-REFERENCE TO RELATED APPLICATIONS

This application is a continuation of application Ser. No. 09/067,188, filed Apr. 27, 1998, now U.S. Pat. No. 5,925, 552, which is a continuation-in-part of Ser. No. 09/001,994, filed Dec. 31, 1997, now U.S. Pat. No. 5,945,319, which is a continuation-in-part of Ser. No. 08/635,187, filed Apr. 25, 1996, now U.S. Pat. No. 5,821,343; a continuation-in-part of Ser. No. 08/984,922, filed Dec. 4, 1997, now U.S. Pat. No. 5,891,506, which is a continuation-in-part of Ser. No. 08/694,535, filed Aug. 9, 1996, now U.S. Pat. No. 5,728, 420; a continuation-in-part of Ser. No. 09/012,056, filed Jan. 22, 1998, now U.S. Pat. No. 6,033,719; and a continuation-in-part of Ser. No. 09/010,906, filed Jan. 22, 1998, now U.S. Pat. No. 5,928,916. All the foregoing patent applications and patents are hereby incorporated by reference herein, each in its respective entirety.

BACKGROUND OF THE INVENTION

For many years, a number of medical devices (e.g., pacemakers, vascular grafts, stents, heart valves, etc.) that contact bodily tissue or fluids of living persons or animals have been developed, manufactured, and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation can diminish the useful lifetime of many devices.

Implantable medical devices also tend to serve as foci for infection of the body by a number of bacterial species. These device-associated infections are promoted by the tendency of these organisms to adhere to and colonize the surface of the device. Consequently, it has been of great interest to physicians and the medical industry to develop surfaces that are less prone in promoting the adverse biological reactions that typically accompany the implantation of a medical device.

One approach for minimizing undesirable biological reactions associated with medical devices is to attach various biomolecules to their surfaces for the attachment and growth of a cell layer which the body will accept. Biomolecules such as growth factors, cell attachment proteins, and cell attachment peptides have been used for this purpose. In addition, biomolecules such as antithrombogenics, antiplatelets, anti-inflammatories, antimicrobials, and the like have also been used to minimize adverse biomaterial-associated reactions.

A number of approaches have been suggested to attach such biomolecules. These approaches typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to substrate surfaces. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10–18 (1972); and Ito et al., "Materials for Enhancing Cell Adhesion by Immobilization of Cell-Adhesive Peptide," J. Biomed. Mat. Res., 25, 1325–1337 (1991).

One type of biomolecule which is commonly coupled to biomaterial surfaces with coupling molecules is protein. Proteins are polypeptides made up of amino acid residues. A protein comprising two or more polypeptide chains is called an oligomeric protein. In general, established coupling procedures couple proteins to substrate surfaces through a protein's lysine amino acid residues which comprise terminal amine moieties. However, not all biomolecules, including some proteins and peptides, comprise terminal amine moieties. In addition, a number of established coupling procedures couple biomolecules which comprise reactive moieties capable of forming bonds with amine moieties to substrate surfaces which comprise terminal amine moieties.

Thus, what is needed are methods for creating terminal amine moieties within biomolecules which lack terminal amine moieties. These newly formed terminal amine moieties can then be used to attach these modified biomolecules to a medical device substrate surface which comprises chemical moieties capable of forming bonds with amine moieties. In addition, methods are needed for creating terminal amine moieties on medical device substrate surfaces which lack terminal amine moieties. These newly formed terminal amine moieties can then be used to attach biomdlecules which comprise chemical moieties capable of forming bonds with amine moieties.

In some cases, covalently coupling of a biomolecule to a biomaterial surface is not desirable. Therefore, there also exists a need for methods which may ionically couple a biomolecule to a biomaterial surface. In fact, ionic coupling techniques have an advantage of not altering the chemical composition of an attached biomolecule, thereby reducing the possibility of destroying the biological properties of an attached biomolecule. Ionic coupling of biomolecules also has an advantage of releasing the biomolecule under appropriate conditions. One example of the ionic attachment of a biomolecule to a surface is set forth in U.S. Pat. No. 4,442,133 to Greco et al. In this case, a tridodecyl methylammonium chloride (TDMAC) coating is used to ionically bind an antibiotic agent.

Another type of biomolecule which is often coupled to biomaterial surfaces is heparin. Heparin, an anionic biomolecule, is of great interest to a number of investigators for the development of non-thrombogenic blood-contact biomaterial surfaces. Heparin, a negatively charged glycosaminoglycan, inhibits blood coagulation primarily by promoting the activity of antithrombin IIII (ATIII) to block the coagulation enzymes thrombin, factor Xa and, to some extent, factors IXa, XIa and XIIa. Surfaces bearing bound heparin have been shown to have anticoagulant activity, therefore, heparinization tends to be a popular technique for improving the thromboresistance of biomaterials. In fact, surface heparinization through an ionic bond is one of the methods used to improve the blood compatibility of a variety of biomaterial surfaces.

The original method of heparinization of surfaces was described by Gott et al., "Heparin Binding On Colloidal Graphite Surfaces", Science, 142, 1297–1298 (1963). They prepared a graphite-benzalkonium-heparin surface and observed good non-thrombogenic characteristics. Others followed, treating materials with quaternary ammonium salts to ionically bind heparin.

Improving on Gott's technique, Grode et al., "Nonthrombogenic Materials via a Simple Coating Process", Trans.

Amer. Soc. Artif. Intern. Organs, 15, 1–6 (1969), eliminated the need for a graphite coating by using tridodecyl methylammonium chloride (TDMAC). Various other quaternary ammonium salts have also been used such as benzalkonium chloride, cetylpyrrdinium chloride, benzyldimethylstearyammonium chloride, beqzylcetyldimethylammonium chloride as set forth in U.S. Pat. No. 5,069,899 to Whitbourne and Mangan.

Glutaraldehyde was even used by some investigators to increase the stability of heparin bound ionically through various ammonium groups. Rather than using a low molecular weight quaternary salt or quaternary amine, many investigators incorporated the quaternizable amine directly onto substrates by copolymerization techniques. In another approach, Barbucci et al., "Surface-Grafted Heparinizable Materials", *Polymer*, 26, 1349–1352 (1985), grafted tertiary amino polymers of poly(amido-amine) structure onto substrates for ionically coupling heparin. The cationic amino groups are capable of interacting electrostatically with the negatively charged groups present in the heparin molecule. They found that the surface's capacity to retain heparin was directly related to the basicity of the grafted cationic amino groups. The greater the basicity of the surface amino groups on the surface, the greater the capacity of the surface has to retain heparin due to a greater percentage of the surface amino groups being protonated at physiological pH.

Current techniques for immobilization of heparin or other charged biomolecules by an ionic bond have been achieved by introducing opposite charges on a biomaterial surface. The main limit to utilization of tonically bonding methods is the creation of opposing charges on either a biomolecule or a biomaterial surface or both. Thus, what is needed are methods for creating charges on a biomolecule or a biomaterial surface or both. These newly formed charges can then be used to attach a biomolecule to a medical device substrate surface.

SUMMARY OF THE INVENTION

The present invention provides methods for attaching a biomolecule to a substrate surface and corresponding medical devices. The present invention provides methods for making a medical device having at least one biomolecule immobilized on a biomaterial surface. One method of the present invention includes converting a biomolecule comprising an unsubstituted amide moiety ($RCONH_2$) into an amine-functional material ($RNH_2$); combining the amine-functional material with a medical device biomaterial surface comprising a chemical moiety (such as, for example, an aldehyde moiety, an epoxide moiety, an isocyanate moiety, a phosphate moiety, a sulphate moiety or a carboxylate moiety) which is capable of forming a chemical bond with the amine-functional material, to bond the two materials together to form an immobilized biomolecule on a medical device biomaterial surface.

The present invention provides another method for making a medical device having at least one biomolecule immobilized on a biomaterial surface. The method includes converting a medical device biomaterial surface comprising an unsubstituted amide moiety ($RCONH_2$) into an amine-functional material ($RNH_2$); combining the amine-functional material with a biomolecule comprising a chemical moiety (such as, for example, an aldehyde moiety, an epoxide moiety, an isocyanate moiety, a phosphate moiety, a sulphate moiety or a carboxylate moiety) which is capable of forming a chemical bond with the amine-functional material, to bond the two materials together to form an immobilized biomolecule on a medical device biomaterial surface.

The present invention also provides a method for making a medical device having at least one biomolecule immobilized on a biomaterial surface. The method includes converting a biomolecule comprising an unsubstituted amide moiety ($RCONH_2$) into an amine-functional material ($RNH_2$); converting the amine-functional material into a guanidino-functional material ($RNHC(NH)NH_2$); combining the guanidino-functional material with a medical device biomaterial surface comprising a chemical moiety (such as, for example, a 1,2-dicarbonyl moiety, a phosphate moiety, a sulphate moiety or a carboxylate moiety) which is capable of forming a chemical bond with the guanidino-functional material, to bond the two materials together to form an immobilized biomolecule on a medical device biomaterial surface.

Additionally, the present invention provides a method for making a medical device having at least one biomolecule immobilized on a biomaterial surface. The method includes converting a medical device biomaterial surface comprising an unsubstituted amide moiety ($RCONH_2$) into an amine-functional material ($RNH_2$); converting the amine-functional material into a guanidino-functional material ($RNHC(NH)NH_2$); combining the guanidino-functional material with a biomolecule comprising a chemical moiety (such as, for example, a 1,2-dicarbonyl moiety, a phosphate moiety, a sulphate moiety or a carboxylate moiety) which is capable of forming a chemical bond with the guanidino-functional material, to bond the two materials together to form an immobilized biomolecule on a medical device biomaterial surface.

Another method of the present invention may be employed to crosslink biomolecules, located in solution or on biomaterial surfaces, comprising both an unsubstituted amide moiety and a chemical moiety capable of forming a chemical bond with an amine moiety. Such a method comprises converting a biomolecule comprising an unsubstituted amide moiety into an amine-functional material; allowing the amine-functional material to combine with the chemical moiety capable of forming a chemical bond with an amine moiety to form a chemical linkage and a crosslinked material. This crosslinked material may be employed as a biomaterial or as a biomaterial coating. In addition, such crosslinked materials may be further modified to contain additional biomolecules. For example, biomolecules comprising a chemical moiety capable of forming a chemical bond with an amine moiety may be attached to residual amine moieties present in or on the surface of the crosslinked material. Alternatively, biomolecules comprising an amine moiety may be attached to residual chemical moieties capable of forming chemical bonds with amine moieties present in or on the surface of the crosslinked material. Additionally, biomolecules coated onto a biomaterial surface may be crosslinked according to still another method of the present invention.

Another method of the present invention may be employed to crosslink biomolecules, located in solution or on biomaterial surfaces, comprising both an unsubstituted amide moiety and a chemical moiety capable of forming a chemical bond with a guanidino moiety. Such a method comprises converting a biomolecule comprising an unsubstituted amide moiety into an amine-functional material; converting the amine-functional material into a guanidino-functional material ($RNHC(NH)NH_2$); allowing the guanidino-functional material to combine with the chemical moiety capable of forming a chemical bond with an guanidino moiety to form a chemical linkage and a crosslinked material. This crosslinked material may be employed as a biomaterial or as a biomaterial coating. In addition, such crosslinked materials may be further modified to contain additional biomolecules. For example, biomolecules comprising a chemical moiety capable of forming a chemical bond with an guanidino moiety may be attached to residual guanidino moieties present in or on the surface of the crosslinked material. Alternatively, Piomolecules comprising a guanidino moiety may be attached to residual chemical moieties capable of forming chemical bonds with guanidino moieties present in or on the surface of the crosslinked material. Additionally, biomolecules coated onto a biomaterial surface may be crosslinked according to still another method of the present invention.

DETAILED DESCRIPTION OF THE INVENTION

As used in the specification and claims hereof, the following terms have the particular meanings and definitions set forth below.

We define the term "chemical bond" appearing herein to be interpreted a broadly to encompass not only covalent bonding and ionic bonding but also interactions, such as, for example, van der Waals forces and hydrogen bonding.

We define the term "biomolecule" appearing herein as a material that engages in a biological activity or which is effective in modulating a biological activity such as eliminating, reducing or enhancing various biological reactions that typically accompany the exposure of human or animal bodily tissues or fluids to a biomaterial. Biomaterial-associated reactions include thrombosis, tissue death, tumor formation, allergic reaction, foreign-body reaction (rejection), inflammatory reaction, infection and cellular attachment and growth. Biomolecules suitable for use in the present invention comprise either an unsubstituted amide moiety, a 1,2-dihydroxy moiety, a 2-aminoalcohol moiety, a 1,2-dicarbonyl moiety, a guanidino moiety, a chemical moiety capable of forming either a covalent bond with an amine moiety (such as, for example, an aldehyde moiety, an epoxide moiety or an isocyanate moiety) or a chemical moiety capable of forming an ionic bond with an amine moiety (such as, for example, a phosphate moiety, a sulphate moiety or a carboxylate moiety), or any possible combination of any one or more of these moieties alone or in combination. In addition, the term "biomolecule" appearing herein may mean any one or more of a biomolecule alone or a combination of different biomolecules.

Generally, biomolecules used according to this invention may be, for example an anticoagulant agent such as heparin and heparan sulfate, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein such as avidin, a glycoprotein, a globular protein, a structural protein, a membrane protein and a cell attachment protein, a peptide such as a glycopeptide, a structural peptide, a membrane peptide and a cell attachment peptide, a proteoglycan, a toxin, an antibiotic agent, an antibacterial agent, an antimicrobial agent such as penicillin, ticarcillin, carbenicillin, ampicillin, oxacillian, cefazolin, bacitracin, cephalosporin, cephalothin, cefuroxime, cefoxitin, norfloxacin, perfloxacin and sulfadiazine, hyaluronic acid, a polysaccharide, a carbohydrate, a fatty acid, a catalyst, a drug, biotin, a vitamin, a DNA segment, a RNA segment, a nucleic acid, a lectin, a ligand and a dye (which acts as a biological ligand).

The biomolecules may be found in nature (naturally occurring) or may be chemically synthesized.

Biomolecules may be chemically synthesized by a number of methods well known to those skilled in the art. For example, a number of methods are know for synthesizing proteins or peptides from amino acids including solution (classical) synthesis methods and solid phase (e.g., SPPS) synthesis methods. Peptides of varying length may also be formed by the partial hydrolysis of very long polypeptide chains of proteins. In addition, proteolytic enzymes such as trypsin, chymotrypsin, and pepsin may be used to cleave specific peptide bonds in proteins and peptides. Furthermore, site-specific oxidative cleavage of peptide bonds using either cupric ions or ferric ions may be used to create peptide and/or polypeptide chains comprising unsubstituted amide moieties. Peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tripeptides and pentapeptides. When there are many amino acids joined together, the structure is termed a polypeptide. In general, polypeptides contain less than 100 amino acid residues and proteins contain 100 or more amino acid residues.

Some biomrolecules are susceptible to conformational changes when brought into contact with a hydrophobic substrate surface. These conformational changes can lead to the exposure of internalized nonpolar groups which may lead to hydrophobic interactions between the biomolecule and the surface. These hydrophobic interactions may cause the exclusion of water molecules that normally surround the biomolecule in solution. This exclusion of water molecules between the biomolecule and the surface strengthens the hydrophobic interaction and may cause further conformational change of the biomolecule. The degree of conformational change a biomolecule experiences may or may not destroy its biological properties. Therefore, one must take into account the hydrophobic nature of the substrate surface when attaching biomolecules which are prone to hydrophobic interactions. In such cases, it is preferred to create a hydrophilic environment on the biomaterial surface, thereby preventing any unwanted hydrophobic interactions between the biomolecule and the surface which may destroy the biological properties of the biomolecule.

There are a number of surface-derivatization techniques (e.g., grafting techniques) well known to those skilled in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

We define the term "glycoprotein" appearing herein as a conjugated protein which contains at least one carbohydrate group which may comprise a 1,2-dihydroxy moiety. A typical glycoprotein contains one or more oligosaccharide units linked to either asparagine amino acid residues by N-glycosidic bonds or serine or threonine amino acid residues by O-glycosidic bonds. The saccharide unit directly bonded to asparagine is typically N-acetylglucosamine, whereas N-acetylgalactosamine tends to be the saccharide unit bonded to serine or threonine residues. Oligosaccharides bound to glycoproteins may contain a variety of carbohydrate units. They tend to be located at sites away from the biologically active site of the protein. Thus, oligosaccharide moieties of glycoproteins can typically be modified with little or no effect on the biological properties of the protein We define the term "glycopeptide" appearing herein as a conjugated peptide which contains at least one carbohydrate group which may comprise a 1,2-dihydroxy moiety. As mentioned earlier, peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tetrapeptides and pentapeptides. When there are many amino acids joined together, the structure is termed a polypeptide. In general, polypeptides contain less than 100 amino acid residues and proteins contain 100 or more amino acid residues.

Glycoproteins and glycopeptides can be chemically synthesized by a number of methods well known to those skilled in the art. For example, glycoproteins and/or glycopeptides can be formed from natural or chemically synthesized proteins and/or peptides by glycosylation, which is the addition of carbohydrate side chains. There are a number of methods well known to those skilled in the art for glycosylating proteins or peptides. For example, side-chain glycosylation can be performed chemically with glycosylbromides for serine (Ser, S) and threonine (Thr, T) amino acid residues and glycosylamines for aspartic acid (Asp, D) amino acid residues, thereby producing glycosylated asparagine (Asn, N) amino acid residues. In addition, glycosylating enzymes can be used to attach carbohydrate side chains to proteins or peptides.

Proteins or peptides, chemically synthesized or naturally occurring, also suitable for use in the present invention comprise an asparagine (Asn, N) amino acid residue or a glutamine (Gln, Q) amino acid residue, both of which comprise an unsubstituted amide moiety. In addition, proteins or peptides, again chemically synthesized or naturally occurring, which are also suitable for use in the present invention comprise a N-terminal serine (Ser, S) amino acid residue, a N-terminal threonine (Thr, T) amino acid residue, or a 5-hydroxylysine (5-hydroxylysine is only known to occur naturally in collagen, but in principal may be placed anywhere in a synthetic peptide or protein) amino acid residue, all of which comprise a 2-aminoalcohol moiety.

Biomolecules or biomaterials of the present invention comprising an unsubstituted amide moiety may be converted into an amine-functional material via a Hofmann rearrangement reaction, also known as a Hofmann degradation of amides reaction. For example, Wirsen et al., "Bioactive heparin surfaces from derivatization of polyacrylamide-grafted LLDPE", *Biomaterials*, 17, 1881–1889 (1996), demonstrated the conversion of unsubstituted amide moieties of a polyacrylamide-low density polyethylene film into primary amine moieties using a Hofmann rearrangement reaction. In another example, Sano et al., "Introduction of functional groups onto the surface of polyethylene for protein immobilization", *Biomaterials*. 14, 817–822 (1993), demonstrated the conversion of unsubstituted amide moieties of a polyacrylamide-high density polyethylene film into primary amine moieties using a Hofmann rearrangement reaction. In another example, Fuller et al., "A new class of amino acid based sweeteners", *J. Am. Chem. Soc.*, 107, 5821–5822 (1985), demonstrated the conversion of an unsubstituted amide moiety of an amino acid into a primary amine moiety using a Hofmann rearrangement reaction. In another example, Loudon et al., "Conversion of aliphatic amides into amines with [1,1-bis(trifluoroacetoxy)iodo] benzene. 1. Scope of the reaction", *J. Org. Chem.*, 49, 4272–4276 (1984), demonstrated the conversion of various unsubstituted amide moieties, including the amide side chain in a glutamine amino acid residue, into primary amine moieties using Hofmann rearrangement reactions.

The Hofmann rearrangement reaction which converts an unsubstituted amide moiety into a primary amine moiety may be carried out with chemical reactants such as, for example, bromine, bromide, bromite, hypobromite, chlorine, chloride, chlorite, hypochlorite, lead tetraacetate, benzyltrimethylammonium tribromide and hypervalent organoiodine compounds such as, for example, [bis (trifluoroacetoxy)iodo]benzene, hydroxy(tosyloxy) iodobenzene and iodosylbenzene. A general discussion of Hofmann rearrangement reactions is contained in *Comprehensive Organic Synthesis*, Volume 6, 800–806, Pergamon Press. For example, Kajigaeshi et al., "An efficient method for the Hofmann degradation of amides by use of benzyltrimethylammonium tribromide", *Chemistry Letters*, 463–464 (1989), described various methods for obtaining amines from amides using the Hofmann rearrangement reaction. These methods include, for example, the use of bromine or chlorine in an alkaline solution, the use of lead tetraacetate in an alcohol solution, the use of [bis (trifluoroacetoxy)iodo]benzene in an aqueous acetonitrile solution, the use of sodium bromite in an alkaline solution, and the use of benzyltrimethylammonium tribromide in an alkaline solution. Catalysts such as, for example, triethylamine, tin(IV) chloride, dibutylstannyl dilaurate or pyridine are sometimes used in a Hofmann rearrangement reaction. Typical solvents include, for example, water, hydroxides, methoxides, alcohols, dimethylformamide, acetonitrle, benzene, carboxylic acids or combinations thereof.

Depending on the chemical reactants, the Hofmann rearrangement reaction may be carried out under acidic, neutral or basic conditions. Although applicants do not wish to be bound by any single theory, it is generally believed that when the reaction is carried out with particular amine forming agents in an aqueous base a N-halo amide intermediate is formed. An isocyanate is then formed from the N-halo amide intermediate. The formed isocyanate then readily hydrolyzes into a primary amine. In contrast, when the reaction is carried out in an alcohol a carbamate is generally formed. The carbamate may then be hydrolyzed into a primary amine. For example, when the reaction of an amide with bromine is carried out in methanol containing sodium methoxide instead of in aqueous base, the product is a carbamate which is easily converted to an amine via hydrolysis. Depending on the reaction conditions, side-reactions such as chain scission, hydrolysis and/or urea formation may occur. However, side-reactions may be minimized by changes in the reaction conditions. For example, changes in the reaction conditions such as pH, time, temperature and/or the amount of amine forming agent may minimize various side-reactions.

In general, the Hofmann rearrangement reaction is carried out with an amine forming agent in amounts ranging from about 0.5 eq. to about 2 eq. based on the amide content of the biomolecule or biomaterial. In addition, the reaction is generally carried out at a temperature between about −10 and about 100 degrees Celsius, preferably from about 0 and about 50 degrees Celsius. Depending on the material, a Hofmann rearrangement reaction may be carried out for as short as a few minutes to as long as many hours. Time, temperature and pH limitations of the present invention are generally governed by the stability of the materials imparted by the Hofmann rearrangement process. Wide latitude may be employed in determining the optimum conditions for a particular system. Such conditions may be determined readily by one skilled in the art by routine experimentation upon examination of the information presented herein.

We define the term "amine forming agent" appearing herein to include any chemical agent or combination of chemical agents capable of forming an amine moiety upon its or their reaction with an unsubstituted amide moiety. Examples of amine forming agents include, for example, bromine, bromide, bromite, hypobromite, chlorine, chloride, chlorite, hypochlorite, lead tetraacetate, benzyltrimethylammonium tribromide and hypervalent organoiodine compounds such as, for example, [bis(trifluoroacetoxy)iodo]benzene, hydroxy(tosyloxy)iodobenzene and iodosylbenzene. Amine forming agents include any of the many possible Hofmann rearrangement reactants. As mentioned above, the term "amine forming agent" appearing herein may mean any one or more of an amine forming agent or a combination of different amine forming agents.

Biomolecules or biomaterials of the present invention comprising, in addition to an unsubstituted amide moiety, a primary amine moiety of which is desired to be left intact and unreacted following coupling may be protected or blocked prior to the Hofmann rearrangement reaction. For example, a protein may comprise both a lysine amino acid residue and, for example, an asparagine amino acid residue. As mentioned earlier, there are a number of established coupling procedures which may couple a protein comprising a lysine amino acid residue to a substrate surface through the protein's lysine amino acid residue. However, a protein's lysine amino acid residues are typically associated with the protein's biologically active site. Therefore, coupling a protein to a substrate surface via a protein's primary amine moiety in the side chain of its lysine amino acid residue may destroy the biological properties of the attached protein. However, a protein's lysine amino acid residue may be protected or blocked by a number of methods well known to those skilled in the art. For example, the amine moiety may be protected using, for example, a tert.butyloxycarbonyl (Boc) group which is typically cleaved with acid, a benzyloxycarbonyl (Z) group which is typically cleaved by hydrogenolysis, a biphenylisopropyloxycarbonyl (Bpoc) group which is typically cleaved with acid, a triphenylmethyl (trityl) group which is typically cleaved with acid, a 9-fluoroenylmethyloxycarbonyl (Fmoc) group which is typically cleaved with base or a blocking group which is pH stable but is cleaved by enzyme-catalyzed hydrolysis. The appropriate amine-blocking group to use to protect the amine moiety will depend highly on the entire sequence of reaction conditions chosen for biomolecule attachment or crosslinking. Following blocking of the amine moiety of the lysine residue, the amide moiety of the asparagine residue may then be converted into an amine moiety via a Hofmann rearrangement reaction. The protein may then be coupled to the substrate via one method of the present invention through the newly formed amine moiety. Following coupling, the amine-blocking group may then be removed, thereby preserving the protein's biological activity. This type of blocking scheme may be employed on biomolecules and/or biomaterials of the present invention which contain amine moieties which are desired to be left intact and unreacted.

Biomaterials of the present invention not comprising unsubstituted amides on their surface may be amidated readily through a number of methods well known in the art. For example, unsubstituted amides may be provided by ceric ion grafting acrylamide to a biomaterial surface as set forth in U.S. Pat. No. 5,344,455 to Keogh et al. Alternatively, for example, a grafted acrylamide-containing polymer may be attached by radiation grafting as set forth in U.S. Pat. No. 3,826,678 to Hoffman et al. There are a number of surface-derivatization techniques (e.g., grafting techniques) well known in the art for creating substrate surfaces comprising unsubstituted amide moieties. For example, techniques based on ceric ion initiation, ozone exposure, corona discharge, UV irradiation and ionizing radiation ($^{60}$Co, X-rays, high energy electrons, plasma gas discharge) are known. In addition, amides can generally be prepared by reaction of ammonia with acid chlorides. This reaction is commonly known as ammonolysis. Acid chlorides are prepared by substitution of —Cl for the —OH group of a carboxylic acid. Reagents commonly used to form acid chlorides from carboxylic acids include thionyl chloride ($SOCl_2$), phosphorus trichloride ($PCl_3$) and phosphorus pentachloride ($PCl_5$). Two amino acids comprising carboxylic acid moieties which may be converted into acid chlorides are aspartic acid (Asp, D) amino acid and glutamic acid (Glu, E) amino acid. The acid chloride moieties may then be converted into amide moieties followed by conversion into amine moieties. In addition, treatment of an ester moiety with ammonia, generally in ethyl alcohol solution, will yield an amide moiety.

Biomolecules or biomaterials suitable for use according to one method of the present invention may comprise at least one negatively charged moiety (also known as an anionic moiety) at physiological pH, such as a phosphate moiety, a sulphate moiety or a carboxylate moiety. A negatively charged moiety is capable of interacting electrostatically with a positively charged moiety (also known as a cationic moiety) thereby forming an ionic chemical bond or linkage.

Biomaterials that do not contain a negative charge on their surfaces may be furnished with a net negative and may be modified readily through a number of methods well known in the art. For example, polyethylene may be exposed to sulfuric acid comprising potassium permanganate thereby creating a negative charge. Other examples of furnishing biomaterials with negatively charged surfaces are taught in U.S. Pat. Nos. 5,344,455 to Keogh et al. and 5,429,618 to Keogh.

Biomolecules or biomaterials suitable for use according to one method of the present invention may comprise at least one positively charged moiety at physiological pH, such as an amine moiety or a guanidino moiety. Biomolecules or biomaterials that do not comprise a positive charge may be furnished with a net positive charge by one method of the present invention. As mentioned earlier, a positively charged moiety is capable of interacting electrostatically with a negatively charged moiety thereby forming an ionic chemical bond or linkage.

Biomolecules or biomaterials suitable for use according to one method of the present invention may comprise at least one epoxide moiety. Epoxide moieties are three-membered rings comprising two carbon atoms and an oxygen atom. An epoxide ring is also known as an oxirane ring. There are a number of techniques well known in the art to produce epoxides. Epoxide moieties are highly reactive due to the ease of opening of the highly strained three-membered ring. An epoxide moiety will react readily with an amine moiety, thereby forming a covalent bond or linkage. The reaction of an epoxide moiety with an amine moiety is well known in the art.

Biomolecules or biomaterials suitable for use according to one method of the present invention may comprise at least one isocyanate moiety. An isocyanate moiety (RNCO) will react readily with an amine moiety, thereby forming a covalent bond or linkage called a urea. There area number of techniques well known in the art to produce isocyanates. In addition, the reaction of an isocyanate moiety with an amine moiety is well known in the art.

We define the term "1,2-dihydroxy moiety" appearing herein as a carbon-carbon bond bearing two adjacent hydroxyl moieties.

We define the term "2-aminoalcohol moiety" appearing herein as a carbon-carbon bond bearing an amine moiety adjacent to a hydroxyl moiety.

The 1,2-dihydroxy moiety and the 2-aminoalcohol moiety are both oxidizable with periodate, which may be provided as periodic acid or salts thereof, such as sodium periodate, potassium periodate, or other alkali metal periodates. Typically, a stoichiometric amount of periodate is used to oxidize the desired number of 1,2-dihydroxy moieties or 2-aminoalcohol moieties to form aldehyde moieties, however less than a stoichiometric amount or more than a stoichiometric amount may be used.

Periodate oxidation of a 1,2dihydroxy moiety or a 2-aminoalcohol moiety is generally carded out in an aqueous solution, preferably an aqueous buffered solution, at a temperature that does not destroy the desired properties of the material. Generally, buffers having a pH in a range between about 4 and about 9 can be used, with a pH between about 6 and about 8 desired for certain pH sensitive materials. Generally, the oxidation is carried out at a temperature between about 0 and about 50 degrees Celsius, and preferably at a temperature between about 4 and about 37 degrees Celsius. Depending on the material, oxidation reactions can be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher treatment temperatures require relatively shorter treatment times. Time and temperature limitations of the present invention are generally governed by the stability of the materials imparted by the oxidation process. Wide latitude may be employed in determining the optimum conditions for a particular system. Such conditions may be determined readily by one skilled in the art by routine experimentation upon examination of the information presented herein.

Subsequent to oxidation, the reaction solution may be stored prior to use at about 4 degrees Celsius. Typically, the storage stability of the reaction solution at a neutral pH or slightly acidic pH may extend between about one and about fourteen days and sometimes even months when stored in the dark.

In general, an aldehyde moiety (RCHO) will react chemically with a primary amine moiety (R'NH$_2$) to form a relatively unstable imine moiety (R'N=CHR). The reaction of an aldehyde moiety with a primary amine moiety which is commonly referred to as a Schiff base reaction may be carried out under the same conditions as described above for the periodate oxidation reaction, which is generally designed to protect a biomolecule from damage. To stabilize the relatively unstable imine linkage, subsequent reductive, alkylation of the imine moiety is carried out using reducing agents (i.e., . stabilizing agents) such as, for example, sodium borohydride, sodium cyanoborohydride, and amine boranes, to form a secondary amine (R'NH—CH$_2$R). This reaction can also be carried out under the same conditions as described above for the periodate oxidation reaction. Typically, however, the coupling and stabilizing reactions are carried out in a neutral or slightly basic solution and at a temperature between about 0 and about 50 degrees Celsius. Preferably, the pH is between about 6 and about 10, and the temperature is between about 4 and about 37 degrees Celsius, for the coupling and stabilizing reactions. These reactions (coupling and stabilizing) may be allowed to proceed for just a few minutes or for many hours. Commonly the reactions are complete (i.e., coupled and stabilized) within 24 hours.

We define the term "guanidino moiety" appearing herein to include guanidine, guanidinium, guanidine derivatives such as (RNHC(NH)NHR'), monosubstituted guanidines, monoguanides, biguanides, biguanide derivatives such as (RNHC(NH)NHC(NH)NHR"), and the like. In addition, the term "guanidino moiety" appearing herein may mean any one or more of a guanide alone or a combination of different guanides.

Guanidine is the imide of urea, or the amidine of carbamic acid. It is a very strong base with a pK$_a$ of 13.5 in water. The great basicity of guanidine is a result of the stability of the conjugated acid (guanidinium) in water. The positive charge on the guanidinium ion can be spread equally among the three nitrogens by resonance. The guanidinium ion is also quite hydrophilic and is well solvated in aqueous media due to the extensive hydrogen bonding of six potential hydrogen bond donors to the solvent. The partial positive charge of the hydrogen bond donors increases their strength for donation to the negative dipole of water. Crystal structures of simple guanidinium derivatives have revealed several common features. First, the C—N single bond length in an alkyl guanidine is typically shorter than the usual C—N single bond length. Usually, the three C—N bonds in the guanidinium group itself are nearly equal in length with an average of 1.33 A. The three N—C—N bond angles are almost always near 120°.

The guanidinium group's features make it a very attractive moiety. For example, its high basicity (a pK$_a$ of 13.5 for guanidinium itself) allows it to remain protonated over a much wider range of pH than does the ammonium group. In fact, at physiological pH, all but a small fraction of the guanidine molecules will exist as positively charged species. The guanidinium group's enhanced hydrogen bonding capabilities, typically two linear hydrogen bonds, allow it to form tighter complexes with anions that are capable of hydrogen bonding. In fact, the guanidinium group may form characteristic pairs of zwitterionic hydrogen bonds which provide binding strength by their charge and structural organization by their arrangement.; Another feature of guanidines are their ability to react with 1,2-dicarbonyl moieties under mild alkaline conditions to form covalent bonds. The reaction of a guanidino moiety and a 1,2-dicarbonyl moiety is similar to a Schiff base reaction (the reaction between an amine moiety and an aldehyde moiety). In some cases, it may be desirable to use a stabilizing agent such as borate ion (BO$_3$) to stabilize the resultant compound.

We define the term "1,2-dicarbonyl moiety" appearing herein as two carbonyl (C=O) groups located on adjacent carbon atoms. A carbonyl group contains a carbon-oxygen double bond.

Biomolecules or biomaterials of the present invention comprising an unsubstituted amide moiety may be modified to comprise guanidino moieties.

The method of the present invention includes converting an unsubstituted amide moiety (RCONH$_2$) into an amine-functional material (RNH$_2$). The amine-functional material is then modified to comprise guanidino moieties by reaction with compounds such as S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-l-guanylpyrazole nitrate and 3,5-dimethyl pyrazole. For example, reaction of amines with O-methylisourea, S-methylisourea, S-ethylthiouronium bromide or S-ethylthiouronium chloride, thereby yielding guanidino moieties, are generally completed after 8 hours at 70 degrees Celsius in a solution of sodium hydroxide (NaOH) at pH 10. Reactions of amines with aminoiminomethanesulfonic acid or cyanamide are generally performed at room temperature. Another example is the reaction of an amine with 2-methyl-1-nitroisourea in water to form a nitroguanidine. The nitro group is then easily removed to form a guanidino moiety by hydrogenolysis.

We define the term "guanidino forming agent" appearing herein to include any chemical agent capable of forming a guanidino moiety upon its reaction with a non-guanidino moiety. Examples of guanidino forming agents include S-ethylthiouronium bromide, S-ethylthiouronium chloride, O-methylisourea, O-methylisouronium sulfate, O-methylisourea hydrogen sulfate, S-methylisothiourea, 2-methyl-i-nitroisourea, aminoiminomethanesulfonic acid, cyanamide, cyanoguanide, dicyandiamide, 3,5-dimethyl-1-guanylpyrazole nitrate and 3,5-dimethyl pyrazole. In addition, the term "guanidino forming agent" appearing herein may mean any one or more of a guanidino forming agent or a combination of different guanidino forming agents.

We define the term "biomaterial" appearing herein as a material that is substantially insoluble in human or animal bodily fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains implanted in or in contact with the body. Biomaterials suitable for use in the present invention comprise either an unsubstituted amide moiety, a 1,2-dihydroxy moiety, a 2-aminoalcohol moiety, a 1,2-dicarbonyl moiety, a guanidino moiety, a chemical moiety capable of forming either a covalent bond with an amine moiety (such as an aldehyde moiety, an epoxide moiety or an isocyanate moiety) or a chemical moiety capable of forming an ionic bond with an amine moiety (such as a phosphate moiety, a sulphate moiety or a carboxylate moiety), or any possible combination of any one or more of these moieties alone or in combination. Additionally, biomaterials comprising both an unsubstituted amide moiety and a 1,2-dihydroxy moiety, a 2-aminoalcohol moiety, or a chemical moiety capable of forming a chemical bond with an amine moiety may by crosslinked, according to one method of the present invention. Also, biomaterials may be fabricated by crosslinking biomolecules, comprising both an unsubstituted amide moiety and a 1,2-dihydroxy moiety, a 2-aminoalcohol moiety, or a chemical moiety capable of forming a chemical bond with an amine moiety, according to another method of the present invention.

Biomaterials or substrates that may be modified according to one method of the present invention include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, human or animal protein or tissue such as bone, skin, teeth, collagen, laminin, elastin or fibrin, organic materials such as wood, cellulose, or compressed carbon, a string, a suture, a fiber, a mesh and other materials such as glass and the like. Biomaterials of the present invention made using these materials may be coated or uncoated, porous or nonporous, permeable and nonpermeable, derivatized or underivatized. We define the term "medical device" appearing herein as a device having surfaces that contact human or animal bodily tissue and/or fluids in the course of their operation. This definition includes within its scope, for example, extracorporeal devices for use in surgery such as blood oxygenators, blood pumps, blood sensors, tubing used to carry blood and the like which contact blood which is then returned to the patient. The definition includes within its scope endoprostheses implanted in blood contact in a human or animal body such as vascular grafts, stents, pacemaker leads, heart valves, and the like that are implanted in blood vessels or in the heart. The definition also includes within its scope devices for temporary intravascular use such as catheters, guide wires, and the like which are placed into the blood vessels or the heart for purposes of monitoring or repair.

One method of the invention may be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind.

The present invention has an object of solving a number of problems associated with the use of medical devices. The present invention includes within its scope methods for attaching biomolecules to biomaterial surfaces for use in medical devices. The present invention further provides methods for fabricating crosslinked biomaterials or crosslinked biomaterial coatings comprising biomolecules.

One preferred method of the present invention may be employed to immobilize a least one biomolecule comprising at least one 2-aminoalcohol moiety on a biomaterial surface comprising at least one unsubstituted amide moiety. The method comprises the steps of: combining a periodate with a biomolecule comprising a 2-aminoalcohol moiety to form an aldehyde-functional material in an aqueous solution having a pH between about 4 and about 9 and a temperature between about 0 and about 50 degrees Celsius;. providing a biomaterial surface comprising an unsubstituted amide moiety, converting the amide moiety into an amine moiety using an amine forming agent to form an amine-functional material; combining the aldehydefunctional material with the amine-functional material to chemically bond the two materials together through an imine moiety; and reacting the imine moiety with a reducing agent to form an immobilized biomolecule on a medical device biomaterial surface through a secondary amine linkage.

Another preferred method of the present invention may be employed to immobilize a least one glycoprotein or glycopeptide comprising at least one 1,2-dihydroxy moiety on- a biomaterial surface comprising at least one unsubstituted amide moiety. The method includes the steps of: combining a periodate with a glycoprotein or glycopeptide comprising a 1,2-dihydroxy moiety to form an aldehyde-functional material in an aqueous solution having a pH between about 4 and about 9 and a temperature between about 0 and about 50 degrees Celsius; providing a biomaterial surface comprising an unsubstituted amide moiety, converting the amide moiety into an amine moiety using an amine forming agent to form an amine-functional material; combining the aldehyde-functional material with the amine-functional material to chemically bond the two materials together through an imine moiety; and reacting the imine -moiety with a reducing agent to form an immobilized glycoprotein or glycopeptide on a medical device biomaterial surface through a secondary amine linkage.

Still another preferred method of the present invention may be employed to immobilize a least one biomolecule comprising at least one epoxide moiety on a biomaterial surface comprising at least one unsubstituted amide moiety. The method includes the steps of: providing a biomaterial surface comprising an unsubstituted amide moiety, converting the amide moiety into an amine moiety using an amine forming agent to form an amine-functional material; combining the epoxide-functional biomolecule with the amine-functional material to chemically bond the two materials together through a covalent linkage.

Yet another preferred method of the present invention may be employed to immobilize a least one biomolecule comprising at least one isocyanate moiety on a biomaterial surface comprising at least one unsubstituted amide moiety. The method includes the steps of: providing a biomaterial surface comprising an unsubstituted amide moiety, converting the amide moiety into an amine moiety using an amine forming agent to form an amine-functional material; combining the isocyanate-functional biomolecule with the amine-functional material to chemically bond the two materials together through a covalent linkage.

Another preferred method of the present invention may be employed to immobilize at least one biomolecule comprising at least one negatively charged moiety, such as a phosphate moiety, a sulphate moiety or a carboxylate moiety, on a biomaterial surface comprising at least one unsubstituted amide moiety. The method includes the steps of: providing a biomaterial surface comprising an unsubstituted amide moiety, converting the amide moiety into an amine moiety using an amine forming agent to form an amine-functional material; combining the negatively charged biomolecule with the amine-functional material to chemically bond the two materials together through an ionic linkage.

One preferred method of the present invention may be employed to immobilize at least one biomolecule comprising at least one chemical moiety which is capable of forming a chemical bond with a guanidino-functional material (such as, for example, a 1,2-dicarbonyl moiety, a phosphate moiety, a sulphate moiety or a carboxylate moiety) on a biomaterial surface comprising at least one unsubstituted amide moiety. The method includes the steps of: providing a biomaterial surface comprising an unsubstituted amide moiety, converting the amide moiety into an amine moiety using an amine forming agent to form an amine-functional material; converting the amine-functional material into a guanidino-functional material using a guanidino forming agent; combining the guanidino-functional material with a biomolecule capable of forming a chemical bond with a guanidino-functional material to chemically bond the two materials together through a chemical linkage.

Still another preferred method of the present invention may be employed to immobilize a least one biomolecule comprising a least one unsubstituted amide moiety on a biomaterial surface comprising a least one chemical moiety which is capable of forming a chemical bond with an amine-functional material (such as, for example, an aldehyde moiety, an epoxide moiety, an isocyanate moiety, a phosphate moiety, a sulphate moiety or a carboxylate moiety). The method includes the steps of: providing a biomolecule comprising an unsubstituted amide moiety, converting the amide moiety into an amine moiety using an amine forming agent to form an amine-functional material; combining the amine-functional material with a biomaterial surface capable of forming a chemical bond with an amine-functional material to chemically bond the two materials together through a chemical linkage.

Yet another preferred method of the present invention may be employed to immobilize a least one biomolecule comprising a least one unsubstituted amide moiety on a biomaterial surface comprising a least one chemical moiety which is capable of forming a chemical bond with a guanidino-functional material (such as, for example, a 1,2-dicarbonyl moiety, a phosphate moiety, a sulphate moiety or a carboxylate moiety). The method includes the steps of: providing a biomolecule comprising an unsubstituted amide moiety, converting the amide moiety into an amine moiety using an amine forming agent to form an amine-functional material; converting the amine-functional material into a guanidino-functional material using a guanidino forming agent; combining the guanidino-functional material with a biomaterial capable of forming a chemical bond with a guanidino-functional material to chemically bond the two materials together through a chemical linkage.

One preferred method of the present invention may be employed to crosslink biomolecules, located in solution or on biomaterial surfaces, comprising at least one unsubstituted amide moiety and at least one chemical moiety which is capable of forming a chemical bond with an amine-functional material (such as, for example, an aldehyde moiety, an epoxide moiety, an isocyanate moiety, a phosphate moiety, a sulphate moiety or a carboxylate moiety). This method comprises the steps of: providing a biomolecule comprising an unsubstituted amide moiety, converting the amide moiety into an amine moiety using an amine forming agent to form an amine-functional biomolecule; allowing the amine-functional biomolecule to combine with a biomolecule capable of forming a chemical bond with an amine-functional biomolecule to chemically bond the two biomolecules together through a chemical linkage, thereby forming a crosslinked material. This crosslinked material may be employed as a biomaterial or as a biomaterial coating. In addition, such crosslinked material may be further modified to contain additional biomolecules. For example, biomolecules comprising aldehyde moieties may be attached to residual amine moieties present in or on the surface of the crosslinked material.

Another preferred method of the present invention may be employed to crosslink biomolecules, located in solution or on biomaterial surfaces, comprising at least one unsubstituted amide moiety and at least one chemical moiety which is capable of forming a chemical bond with a guanidino-functional material (such as, for example, a 1,2-dicarbonyl moiety, a phosphate moiety, a sulphate moiety or a carboxylate moiety). This method comprises the steps of: providing a biomolecule comprising an unsubstituted amide moiety, converting the amide moiety into an amine moiety using an amine forming agent to form an amine-functional biomolecule; converting the amine-functional biomolecule into a guanidino-functional biomolecule using a guanidino forming agent; allowing the guanidino-functional biomolecule to combine with a biomolecule capable of forming a chemical bond with an guanidino-functional biomolecule to chemically bond the two biomolecules together through a chemical linkage, thereby forming a crosslinked material. This crosslinked material may be employed as a biomaterial or as a biomaterial coating. Additionally, such crosslinked material may be further to modified to contain additional biomolecules. For example, biomolecules comprising 1,2-dicarbonyl moieties may be attached to residual guanidino moieties present in or on the surface of the crosslinked material.

One example of a biomolecule of the present invention is collagen. Collagen, which is found in connective tissue, has special amino acids, one of which is 5-hydroxylysine which may be oxidized with a source of periodate, which may be provided as periodic acid or salts thereof, such as sodium periodate, potassium periodate, or other alkali metal periodates, to form a pendant aldehyde moiety. The resultant aldehyde moieties may be used to crosslink the collagen through bonds formed between the aldehydes and amines, for example, lysine amino acid residues or modified asparagine amino acid residues, contained on neighboring collagen molecules. The resultant imine bonds may then be reduced using a mild reducing agent like sodium borohydride, sodium cyanoborohydride, or amine boranes. These crosslinks may endow the collagen biomaterial or biomaterial coating with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the collagen to control its physical and biological properties.

The aldehyde moieties formed by oxidation of collagen may also be used to couple a variety of amine-containing biomolecules to the crosslinked collagen biomaterial or biomaterial coating. Also, the ability to create aldehyde moieties along collagen molecules enables them to be covalently attached to amine containing biomaterial surfaces. Such collagen-coated biomaterial surfaces may be used, for example, as cell seeding surfaces, cell binding surfaces, cell separating surfaces, tissue fixation, collagen-coated stents, collagen-coated vascular grafts or collagen glues.

Other biomolecules, such as structural proteins, may be crosslinked to form a material that may be used as a biomaterial or a biomaterial coating. Also, additional biomolecules, as described herein, may be attached to residual amine moieties contained in or on a fabricated crosslinked biomaterial or biomaterial coating, as described herein. Alternatively, amine containing biomolecules may be attached to residual aldehyde moieties contained in or on a fabricated crosslinked biomolecule biomaterial or biomaterial coating, as described herein.

An example of a glycoprotein that can be used in a number of aspects of the present invention is fibrin(ogen). Fibrin(ogen), which is a structural protein, has oligosaccharides which can be oxidized with a source of periodate, which can be provided as periodic acid or salts thereof, such as sodium periodate, potassium periodate, or other alkali metal periodates, to form a pendant aldehyde moiety. The resultant aldehyde moieties can be used to crosslink the fibrin(ogen) through bonds formed between the aldehydes and amines contained on neighboring fibrin(ogen) molecules. The resultant imine bonds can then be reduced using a mild reducing agent like sodium borohydride, sodium cyanoborohydride, or amine boranes. These crosslinks can endow the fibrinogen and/or fibrin (thrombin polymerized fibrinogen) biomaterial or biomaterial coating with desirable biological and/or physical properties such as mechanical strength, anti-immunogenicity, biostability, among others, without the use of a coupling agent. Thus, the method of the present invention eliminates the need for using glutaraldehyde, a commonly used cytotoxic coupling agent, to crosslink the fibrinogen and/or fibrin to control its physical and biological properties.

The aldehyde moieties formed by oxidation of fibrin (ogen) can also be used to couple a variety of amine-containing biomolecules to the crosslinked fibrin(ogen) biomaterial or biomaterial coating. Also, the ability to create aldehyde moieties along fibrin(ogen) molecules enables them to be covalently attached to amine containing biomaterial surfaces. Such fibrinogen/fibrin coated biomaterial surfaces can be used, for example, as cell seeding surfaces, cell binding surfaces, cell separating surfaces, fibrinogen/fibrin-coated stents, fibrinogen/fibrin-coated vascular grafts or fibrinogen/fibrin glues.

Although the examples described below relate generally to treatment also of polymeric films or tissue culture plates as substrate surfaces, those examples are merely illustrative and are intended to limit in no way the scope of the present invention.

EXAMPLE 1

Periodate Oxidation of a Peptide Containing an N-terminal Serine Amino Acid Residue Two biomolecules, a tripeptide made of three serine amino acid residues and a dipeptide made of two lysine amino acid residues, both obtained from Sigma Chemical Co. (St. Louis, Mo.), were incubated in sodium metaperiodate ($NaIO_4$) also obtained from Sigma Chemical Co. (St. Louis, Mo.). The tripeptide, 0.90 mmoles, was incubated in the dark while shaking at room temperature for 3 hours in 10 ml deionized water containing 1.2 mmoles $NaIO_4$. The resultant solution, 2.5 ml, was added to 2 ml of a solution containing 0.8 g NaOH, 0.2 g 4-amino-3-hydrazino-5-mercapto-1,2,4 -triazole, which is available under the trade designation PURPALD from Sigma Chemical Co. (St. Louis, Mo.), in 20 ml deionized water, and shaken vigorously for 15 minutes at room temperature. The dipeptide, 0.72 mmoles, was incubated in the dark while shaking at room temperature for 3 hours in 10 ml deionized water containing 1.2 mmoles $NaIO_4$. The resultant solution, 10 ml (note that this amount is four times the amount used for the tripeptide), was then added to 2 ml PURPALD solution and shaken vigorously for 15 minutes at room temperature. The resultant solutions were then analyzed spectrophotometrically at 550 nm. Dickinson and Jacobsen, *Chem. Commun.*, 1719 (1970), described the specific and sensitive reaction of aldehydes with PURPALD to yield purple-to-magentacolored 6-mercapto-5-triazolo-(4,3-b)-s-tetrazines which can be measured spectrophotometrically at 550 nm. Sample absorbances obtained at 550 nm were 0.04 for the dipeptide and 1.81 for the tripeptide, which indicates that only the tripeptide which contained an N-terminal serine was successfully oxidized using periodate. The dipeptide of the two lysine amino acids lacked a 2-aminoalcohol moiety, that is a carbon-carbon bond bearing an amine moiety adjacent to a hydroxyl moiety.

EXAMPLE 2

Periodate Oxidation of a Peptide Containing an N-terminal Threonine Amino Acid Residue A biomolecule, a dipeptide made of N-terminal threonine and leucine amino acid residues obtained from Sigma Chemical Co. (St. Louis, Mo.), was incubated in sodium metaperiodate ($NaIO_4$) also obtained from Sigma Chemical Co. (St. Louis, Mo.). The dipeptide, 4.3 mmoles, was incubated in the dark while shaking at room temperature for 3 hours in 10 ml deionized water containing 1.2 mmoles $NaIO_4$. The resultant solution, 10 ml, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.62 indicating the periodate had successfully oxidized the N-terminal threonine amino acid present in the dipeptide, thereby forming an aldehyde moiety.

EXAMPLE 3

Periodate Oxidation of a Peptide Containing an N-terminal Serine Amino Acid Residue A biomolecule, a pentapeptide made of N-terminal serine, aspartic acid, glycine, arginine, and glycine amino acid residues obtained from Sigma Chemical Co. (St. Louis, Mo.), was incubated in sodium metaperiodate ($NaIO_4$) also obtained from Sigma Chemical Co. (St. Louis, Mo.). The pentapeptide, 0.01 mmoles, was incubated in the dark while shaking at room temperature for 3 hours in 2 ml deionized water containing 0.23 mmoles $NaIO_4$. The resultant solution, 10 ml, was added to 2 ml of the PURPALD solution described in Example 1 and shaken vigorously for 15 minutes at room temperature. After the 15 minutes of shaking at room temperature, the resultant solution was analyzed spectrophotometrically at 550 nm. Sample absorbance obtained at 550 nm was 0.74, indicating the periodate had successfully oxidized the N-terminal serine amino acid residue present in the pentapeptide, thereby forming an aldehyde moiety.

EXAMPLE 4

Oxidation of Collagen

The biomolecule, mouse collagen, type IV, obtained from Sigma Chemical Co. (St. Louis, Mo.), was oxidized with sodium metaperiodate ($NaIO_4$); Collagen type IV is known to mediate the attachment of epithelial, endothelial, myoblasts and nerve cells in vivo and in vitro. Two collagen solutions were prepared by i) mixing half a vial of collagen with 56 mg $NaIO_4$ in 5 ml deionized water and ii) mixing half a vial of collagen in 5 ml deionized water. Both solutions were incubated in the dark for 2 hours while shaking at room temperature. The resultant solutions, 100 ml of each, were added to 2 ml the PURPALD solution described in Example 1 and shaken vigorously for 30 minutes at room temperature. After the 30 minutes of shaking at room temperature, the resultant solutions were analyzed spectrophotometrically at 550 nm. The PURPALD solution was used as the blank. Sample absorbances obtained at 550 nm were 0.03 for nonoxidized collagen and 0.25 for oxidized collagen, indicating the periodate had successfully oxidized the collagen, thereby forming aldehyde moieties.

EXAMPLE 5

Attachment of Periodate Oxidized Biomolecules to Aminated Substrates

One method for creating amines on substrate surfaces entails grafting substrate surfaces with acrylamide (Mm) and N-(3-aminopropyl)methacrylamide (APMA) monomers using ceric ($Ce^{IV}$) ions. The $Ce^{IV}$ ions create free radicals on ozone treated silicone and polystyrene surfaces and untreated polyurethane surfaces which initiate the graft copolymerization of the acrylamides. The amount of surface amination (the graft copolymerization of APMA and Mm) that takes place on the substrate surface may be measured via staining with ponceau S dye, a negatively charged dye molecule. This dye ionically associates with the primary amines on the aminated surface. Following grafting, a periodate oxidized biomolecule may be coupled to the amine containing derivatized substrate surface. A 2-aminoalcohol-containing biomolecule is first oxidized with sodium metaperiodate ($NaIO_4$) forming a reactive aldehyde moiety. The aldehyde moiety is then used to covalently attached the biomolecule to the primary amine moiety present on the substrate surface. Sodium cyanoborohydride ($NaCNBH_3$) is then used to stabilize the imine linkages. Specific procedures required for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposed the flowing oxygen to an 8000V electrical potential. Following ozone treatment, the plates were soaked in nitrogen purged deionized water for 30 minutes at room temperature. Following the 30 minute soak in nitrogen purged deionized water, the plates were grafted with acrylatmide (Mm) and N-(3-aminopropyl) methacrylamide (APMA) monomers using $Ce^{IV}$ ion. The grafting solution-consisted of 40 g AAm, 10 g APMA, 50 g deionized water solution, and 20 g $Ce^{IV}$ ion solution. The $Ce^{IV}$ ion solution consisted of 2.74 g ceric ammonium nitrate and 3.15 g nitric acid in 50 ml deionized water. The plates were allowed to graft for 3 hours in a 65 degrees Celsius nitrogen purged oven. Following grafting, the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. As the results demonstrate, the surface-derivatized plates contain primary amines on their surfaces.

The 2-aminoalcohol moiety of a peptide may be oxidized using the procedure of Example 1. Sodium cyanoborohydride (1 mg/ml) then is added to the oxidized peptide solution. The resultant solution then is immediately added to each of the amine containing surface-derivatized tissue culture plate wells (approximately 1 ml solution/well). The oxidized peptide is then incubated in the derivatized tissue culture plate wells overnight at room temperature. Following incubation, the wells are vigorously rinsed with phosphate buffered saline (PBS) solution.

Polyurethane film samples were cut into 1.4 cm diameter disks. Sample disks were grafted with Mm and APMA monomers using $Ce^{IV}$ ion. The sample disks were allowed to graft 1 hour at room temperature. Following grafting, the sample disks were rinsed vigorously with deionized water. Again, the 2-aminoalcohol moiety of a peptide can be oxidized as previously described. Sample disks are then exposed to the oxidized peptide solution. Sodium cyanoborohydride is then added (1 mg/ml) and the resultant solution and sample disks are incubated overnight at room temperature. Following incubation, the polyurethane sample disks are vigorously rinsed with PBS.

EXAMPLE 6

Crosslinking of Collagen

A biomolecule such as collagen, type IV, may be oxidized with sodium metaperiodate ($NalO_4$). A collagen solution may be prepared by mixing half a vial of collagen with 56 mg $NalO_4$ in 5 ml deionized. The solution may be incubated in the dark for 2 hours while shaking at room temperature. The oxidized collagen molecules are then allowed to form crosslinks, thereby bonding the molecules together through imine moieties. An imine moiety is formed from an aldehyde moiety of one collagen molecule reacting with an amine moiety of a neighboring collagen molecule. The imine linkages are then stabilized by reacting the imine moieties with sodium cyanoborohydride (1 mg/ml) to form secondary amine linkages. The resultant crosslinked material may be employed as a biomaterial or as a biomaterial coating.

EXAMPLE 7

Periodate Oxidation of Bovine Fibrinogen

The glycoprotein bovine fibrinogen obtained from Sigma Chemical Co. (St. Louis, Mo.) was incubated in sodium metaperiodate ($NalO_4$) also obtained from Sigma Chemical Co. (St. Louis, Mo.). The following four fibrinogen solutions were prepared to investigate the oxidation of fibrinogen with varying amounts of periodate: (1) 0.03 mM fibrinogen, 0.2 mM $NalO_4$, 0.008 M $Na_2HPO_4$, 0.002 M $KH_2PO_4$, 0.14 M NaCl, pH 7.4; (2) 0.03 mM fibrinogen, 0.1 mM $NalO_4$, 0.008 M $Na_2HPO_4$, 0.002 M $KH_2PO_4$, 0.14 M NaCl, pH 7.4; (3) 0.03 mM fibrinogen, 0.05 mM $NalO_4$, 0.008 M $Na_2HPO_4$, 0.002 M $KH_2PO_4$, 0.14 M NaCl, pH 7.4; and (4) 0.03 mM fibrinogen, 0.008 M $Na_2HPO_4$, 0.002 M $KH_2PO_4$, 0.14 M NaCl, pH 7.4. The four fibrinogen solutions were incubated in the dark for 2 hours while shaking at room temperature. The resultant solutions, 500 µl of each, were added to 2 ml of a solution containing 0.8 g NaOH, 0.2 g 4-amino-3-hydrazino-5-mercato-1,2,4-triazole, which is available under the trade designation PURPALD from Sigma Chemical Co. (St. Louis, Mo.), in 20 ml deionized water, and shaken vigorously for 15 minutes at room temperature. Dickinson and Jacobsen, *Cem. Commun.*, 1719 (1970), described the specific and sensitive reaction of aldehydes with PURPALD to yield purple-to-magenta-colored 6-mercapto-s-triazolo-(4,3-b)-s-tetrazines. After the 15 minutes of shaking at room temperature, the resultant solutions were analyzed spectrophotometrically at 550 nm.

Sample 4 was used as the blank. Sample absorbances obtained at 550 nm were 0.54 for sample 1, 0.53 for sample 2 and 0.51 for sample 3, which indicates that for all samples the fibrinogen was successfully oxidized forming aldehyde groups.

EXAMPLE 8

Periodate Oxidation of Bovine Vitronectin

The glycoprotein bovine vitronectin obtained from Sigma Chemical Co. (St. Louis, Mo.) was incubated in sodium metaperiodate ($NalO_4$) also obtained from Sigma Chemical Co. (St. Louis, Mo.). The following two vitronectin solutions were prepared: (1) 0.001 mM vitronectin, 0.05 M $NalO_4$ and (2) 0.001 mM vitronectin. Both solutions were incubated in the dark for 2 hours while shaking at room temperature. The resultant solutions, 100 µl of each, were added to 2 ml PURPALD solution described in Example 1, and shaken vigorously for 30 minutes at room temperature. After the 30 minutes of shaking at room temperature, the resultant solutions were analyzed spectrophotometrically at 550 nm. The PURPALD solution was used as the blank. Sample absorbances obtained at 550 nm were 0.09 for sample 1 and 0.04 for sample 2, which indicated that vitronectin was successfully oxidized with forming aldehyde groups.

EXAMPLE 9

Periodate Oxidation of Bovine Fibronectin

The glycoprotein bovine fibronectin obtained from Sigma Chemical Co. (St. Louis, Mo.) was incubated in sodium metaperiodate ($NalO_4$) also obtained from Sigma Chemical Co. (St. Louis, Mo.). The following two fibronectin solutions were prepared: (1) 0.002 mM fibronectin, 0.05 M $NalO_4$, 0.5 M NaCl, 0.05 M Tris, pH 7.5; and (2) 0.002 mM fibronectin, 0.5 M NaCl, 0.05 M Tris, pH 7.5. Both solutions were incubated in the dark for 2 hours while shaking at room temperature. The resultant solutions, 100 µl of each, were added to 2 ml PURPALD solution describe in Example 1 and shaken vigorously for 30 minutes at room temperature. After 30 minutes of shaking at room temperature, the resultant solutions were analyzed spectrophotometrically at 550 nm. Following an initial analysis, sample 1 was observed to contain to many aldehydes to measure. Therefore, sample 1 was diluted 1:50 in deionized water to achieve a measurable amount of aldehydes contained in the sample solution. The PURPALD solution was used as the blank. Sample absorbances obtained at 550 nm were 0.81 for sample 1 and 0.0 for sample 2, which indicate that the fibronectin in sample 1 was successfully oxidized forming aldehyde groups. Fibronectin in sample 2 was not oxidized due to the omission of periodate.

EXAMPLE 10

Attachment of Fibronectin to Aminated Substrates

Fibronectin was covalently attached to a substrate surface. The attachment technique began with the graft copolymerization of acrylamide (Mm) and N-(3-aminopropyl) methacrylamide (APMA) monomers onto an ozone treated polystyrene tissue culture plate with ceric ($Ce^{IV}$) ions. The $Ce^{IV}$ ions create free radicals on the ozone treated surface which initiate the graft copolymerization of the acrylamides. The amount of surface amination (the graft copolymerization of APMA and Mm) that took place on the substrate surface was measured via staining with ponceau S dye, a negatively charged dye molecule. Following grafting, fibronectin was coupled to the amine containing derivatized substrate surface. Fibronectin was first oxidized with sodium metaperiodate ($NaIO_4$) forming reactive aldehyde groups. These aldehyde groups were then used to covalently attached fibronectin to the primary amino groups present on the substrate surface. Sodium cyanoborohydride ($NaCNBH_3$) was then used to stabilize the imine linkages. The specific procedures for each of these steps are described below.

Polystyrene 24 well tissue culture plates were ozone treated by placing the culture plates in an ozone reaction vessel for 30 minutes while oxygen, which contained ozone, was flowing at a rate of 1.3 $cm^3$/min. The oxygen containing ozone was created by flowing the oxygen through a corona discharge apparatus, which exposes the flowing oxygen to an 8000V electrical potential. Following ozone treatment, the plates were soaked in nitrogen purged deionized water for 30 minutes at room temperature. Following the 30 minute soak in nitrogen purged deionized water, the plates were grafted with acrylamide (AAm) and N-(3-aminopropyl)methacrylamide (APMA) monomers (Eastman Kodak Co., Rochester, N.Y.) using ammonium cerium (IV) nitrate (Aldrich Chemical Co., Milwaukee, Wis.). The grafting solution consisted of 11.2 M AAm, 1.1 M APMA, 400 mM nitric acid and 40 mM ammonium cerium (IV) nitrate in deionized water. The plates were allowed to graft for 3 hours in a 65° C. nitrogen purged oven. Following grafting the plates are rinsed vigorously with deionized water. The grafted plates were then tested with ponceau S dye. Following staining, the ponceau S dye was released from the surface using a 1% sodium dodecyl sulphate (SDS) solution and quantified spectrophotometrically at 520 nm. Sample absorbances obtained at 520 nm were 0.00 for nonderivatized plates and 1.44 for surface-derivatized plates. As the results demonstrate, the surface-derivatized plates contain primary amines on their surfaces.

Bovine fibronectin obtained from Sigma Chemical Co. (St. Louis, Mo.) was then incubated in sodium metaperiodate ($NaIO_4$) also obtained from Sigma Chemical Co. (St. Louis, Mo.). The following fibronectin solution was prepared: 0.002 mM fibronectin, 0.05 M $NaIO_4$, 0.5 M NaCl, 0.05 M Tris, pH 7.5. The solution was incubated in the dark for 2 hours while shaking at room temperature. Sodium cyanoborohydride (1 mg/ml) was then added to the fibronectin solution. The resultant solution was immediately added to each of the amine containing surface-derivatized tissue culture plate wells (approximately 1 ml solution/well). The fibronectin solution incubated in the derivatized tissue culture plate wells overnight at room temperature. Following incubation, the wells were then vigorously rinsed with phosphate buffered saline (PBS) solution. The attachment of fibronectin to the amine containing surface-derivatized tissue culture plate surfaces was assessed using toluidine blue dye, a positively charged dye molecule. This dye ionically associates with the negative charges on a substrate surface. Therefore, the binding of toluidine blue dye to the fibronectin-derivatized surface is due to fibronectin's negative charges. The wells of each plate were filled with a 1% toluidine blue dye in deionized water solution. After a 5 minute incubation at room temperature, the dye solution was removed and the wells were thoroughly rinsed with PBS. The surface associated dye in each well was then eluted by mechanically shaking the plates in a 1% SDS in deionized water solution overnight. The amount of dye eluted from the wells was then determined spectrophotometrically at 630 nm. Sample absorbances obtained at 630 nm were 0.05 for the nonderivatized sample plate, 0.54 for the AAm/APMA-derivatized sample plate and 1.83 for the fibronectin-derivatized sample plate, which indicate that the fibronectin was successfully oxidized and then covalently attached to the substrate surface.

EXAMPLE 11

ELISA and Cellular Adherence to Fibronectin Coupled Surfaces

Polyurethane in the form of Pellethane 2363–55D was obtained from Dow Chemical Co. (Midland, Mich.) and extruded into film. The film was then cut into 1 $cm^2$ sample disks. Sample disks were then cleansed with ethanol and surface grafted with Mm and APMA monomers using $Ce^{IV}$ ion. The grafting solution consisted of 11.2 M AAm, 1.1 M APMA, 400 mM nitric acid and 40 mM ammonium cerium (IV) nitrate in deionized water. The sample disks were placed into the grafting solution and allowed to graft for 1 hour at room temperature. Following grafting, the sample disks were thoroughly washed with deionized water. Fibronectin was then coupled to the resultant APMA/AAm surface-derivatized sample disks via two methods.

The first method or peroxide method included the oxidation of fibronectin by sodium metaperiodate. Fibronectin (0.1 mg/ml) was exposed in the dark to a 1 $\mu$g/ml sodium metaperiodate in deionized water solution for 3 hours at room temperature. The APMA/AAm-derivatized sample disks were then placed into the oxidized fibronectin solution for 24 hours at room temperature. Sample disks were then thoroughly rinsed with deionized water. The samples were then incubated for 24 hours at room temperature in a 3 mg/ml sodium cyanoborohydride in deionized water solution. Sample disks were then thoroughly rinsed with deionized water.

The second method used glutaraldehyde as a coupling agent. The method included soaking the APMA/AAm-derivatized sample disks in a 2% glutaraldehyde in deionized water solution for 2 hours at room temperature. Sample disks were then thoroughly rinsed with deionized water. Following rinsing, the sample disks were then incubated in a 0.1 mg/ml fibronectin in deionized water solution for 24 hours at room temperature. Sample disks were then thoroughly rinsed with deionized water. The sample disks were then incubated for 24 hours at room temperature in a 3 mg/ml sodium cyanoborohydride in deionized water solution. Sample disks were then thoroughly rinsed with deionized water.

An enzyme linked immunosorbent assay (ELISA) was then performed to determine the ability of an antibody to recognize the fibronectin which had been coupled to the sample surfaces. Sample disks were washed for 20 minutes at room temperature with wash buffer (pH 7.4) consisting of 10 mM Tris, 0.15 M NaCl and 0.05% Tween. Sample disks were then incubated at 37° C. for 30 minutes in blocking buffer (pH 7.4) consisting of 1 0 mM Tris, 0.15 M NaCl, 0.05% Tween and 0.05% gelatin followed by three 10 minute washes with wash buffer. Next, sample disks were incubated at 37° C. for 1 hour in a primary antibody solution (pH 7.4) consisting of 10 mM Tris, 0.15 M NaCl and 2 $\mu$g/ml mouse monoclonal anti-fibronectin antibody (Sigma Chemical Co., St. Louis, Mo.). Sample disks were then rinsed thrice (10 minutes per wash) with wash buffer. Next, sample disks were incubated at 37° C. for 1 hour in a peroxidase-labeled secondary antibody solution (pH 7.4) consisting of 10 mM Tris, 0.15 M NaCl and 0.5 ng/ml anti-mouse IgG peroxidase antibody conjugate (Sigma Chemical Co., St. Louis, Mo.). Sample disks were then rinsed thrice (10 minutes per wash) with wash buffer. Sample disks were then incubated for 15 minutes at room temperature in a phosphate-citrate buffer (pH 5.0) containing 0.4 mg/ml o-phenyidiamine dihydrochloride and 0.2 µl/ml 30% hydrogen peroxide. The phosphate-citrate buffer consisted of 50 mM dibasic sodium phosphate and 25 mM citric acid in deionized water. Following the 15 minute incubation, the peroxide reaction was stopped with 3 M HCl and the absorbance of the resultant solution was measured spectrophotometrically at 492 nm. The APMAAAm-derivatized sample disks were used as controls for this experiment. Sample absorbances obtained from the spectrophotometric analysis were 0.016±0.038 for APMA/Am-derivatized samples which contained glutaraldehyde coupled fibronectin and 0.204±0.068 for APMA/AAm-derivatized samples which contained periodate oxidized fibronectin. The results indicate that the periodate oxidation method was more successful at attaching fibronectin to the sample surfaces.

A cellular adherence assay was also performed to determine the ability of cells to adhere to fibronectin-derivatized sample surfaces. Sample disks were incubated for 1 hour at 37° C. in a blocking buffer consisting of 2 mg/ml ovalbumin in phosphate buffered saline (PBS), pH 7.4. Mouse fibroblasts (C3T3) obtained from American Type Culture Collection (Rockville, Md.) and maintained in Dulbecco's modified Eagie's medium (DMEM) supplemented with 10% fetal bovine serum were harvested using trypsin:EDTA and resuspended in serum-free DMEM containing 2 mg/ml ovalbumin. The cells were then washed twice, counted and resuspended to a final density of $5 \times 10^4$ cells/ml in serum-free DMEM containing 2 mg/ml ovalbumin. Sample disks were then incubated in the cell suspension for 1 hour at 37° C. Nonadherent cells were removed by a PBS wash. Sample disks were then fixed in 3% paraformaldehyde solution for 30 minutes. Adherent cells were then stained with a staining solution consisting of 1% toluidine blue dye and 3% paraformaldehyde in PBS. Following staining, sample surfaces were then examined for cellular adherence using a light microscope. Upon examination, APMA/Mm-derivatized samples and APMA/AAm-derivatized samples which contained glutaraldehyde coupled fibronectin appeared to have no adherent cells. In contrast, cells appeared adherent to APMA/AAm-derivatized samples which contained periodate oxidized fibronectin.

EXAMPLE 12

Crosslinking of Fibrinogen

Porcine fibrinogen obtained from Sigma Chemical Co. (St. Louis, Mo.) was incubated in sodium metaperiodate ($NalO_4$) also obtained from Sigma Chemical Co. (St. Louis, Mo.) and sodium cyanoborohydride ($NaCNBH_3$) obtained from Aldrich Chemical Co. (Milwaukee, Wis.). The following fibrinogen solution was prepared: 0.03 mM fibrinogen, 0.02 M $NalO_4$, 0.02 M $NaCNBH_3$, 0.008 M $Na_2HPO_4$, 0.002 M $KH_2PO_4$, 0.14 M NaCl, pH 7.4. The solution was then shaken vigorously and placed into a 24 well tissue culture plate (approximately 1 ml of fibrinogen solution/well). The plate was then incubated in the dark for 2 hours while shaking at room temperature. After 2 hours, the solution was observed to have become cloudy and very viscous indicating the fibrinogen had crosslinked. The sample was then shaken for an additional 22 hours in the dark. Following incubation, the crosslinked fibrinogen was tested for residual aldehydes using the PURPALD solution describe in Example 1. The results of the PURPALD assay demonstrated few residual aldehydes were present which indicated the formation of covalent crosslinks between the aldehydes and the amines present along the fibrinogen molecules.

The following bovine fibrinogen (Sigma Chemical Co., St. Louis, Mo.) solution was prepared: 0.02 mM fibrinogen, 0.008 M $Na_2HPO_4$, 0.002 M $KH_2PO_4$, 0.14 M NaCl, pH 7.4. Following preparation, the solution was divided into four equal portions. Sodium metaperiodate (0.05 mM) was then added to samples 3 and 4. All four fibrinogen solutions were then incubated in the dark for 2 hours while shaking at room temperature. Next, 0.02 mM $NaCNBH_3$ was added to samples 2 and 4. Again, all four fibrinogen solutions were allowed to react for 2 hours while shaking at room temperature. The samples, 50 µl of each, were then placed into 450 µl of SDS-PAGE buffer solution consisting of 62.5 mM Tris-HCL, 5% b-mercaptoethanol, 10% glycerol and 2.3% SDS. Samples were then boiled for 3 minutes. The; samples, 10 µl of each, were then loaded onto a 4–15% gradient gel and SDS-PAGE was performed according to the procedures described in O'Farrell, "High Resolution Two-dimensional Electrophoresis of Proteins", *J. Biol. Chem.* 250, 4007–4021 (1974). Following electrophoresis, the gel was stained with Coomassie Brilliant Blue, and the identity of the eluted proteins was determined by reference to molecular weight standards included on the gel. The results from SDS-PAGE indicated that the fibrinogen molecules in sample 4 had formed stable covalent crosslinks. In contrast, the results demonstrated that the fibrinogen molecules in the samples which contained no $NalO_4$ had formed no crosslinks.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of forming a coating on a surface of a medical device, the coating imparting improved biocompatibility characteristics to the surface, the method comprising the steps of:
   (a) providing the medical device, the device having a biomaterial disposed on or forming a surface thereof, the biomaterial comprising an unsubstituted amide moiety;
   (b) combining the amide moiety with an amine forming agent to form an amine-functional surface;
   (c) combining the amine-functional surface with a guanidino forming agent to form a guanidino-functional surface;
   (d) providing a biomolecule, the biomolecule comprising a chemical moiety selected from the group consisting of an aldehyde moiety formed by combining a periodate with a 2-aminoalcohol moiety, an aldehyde moiety formed by combining a periodate with a 1,2-dihydroxy moiety, an epoxide moiety, an isocyanate moiety, a 1,2-dicarbonyl moiety, a phosphate moiety, a sulphate moiety and a carboxylate moiety; and
   (e) combining the chemical moiety with the guanidino-functional surface to form a chemical bond, the chemical bond immobilizing the biomolecule on the surface, the immobilized biomolecule forming the coating.

2. The method of claim 1 comprising the further step of combining a stabilizing agent with the chemical bond.

3. The method of claim 2 wherein the stabilizing agent is a borate ion.

4. The method of claim 1 wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

5. A method of forming a coating on a surface of a medical device, the method comprising the steps of:
  (a) providing the medical device, the device having a biomaterial disposed on or forming a surface thereof, the biomaterial comprising an unsubstituted amide moiety;
  (b) combining the amide moiety with an amine forming agent to form an amine-functional surface;
  (c) combining the amine-functional surface with a guanidino forming agent to form a guanidino-functional surface;
  (d) providing a biomolecule, the biomolecule comprising a chemical moiety selected from the group consisting of a 1,2-dicarbonyl moiety, a phosphate moiety, a sulphate moiety, and a carboxylate moiety; and
  (e) combining the chemical moiety with the guanidino-functional surface to form a chemical bond, the chemical bond immobilizing the biomolecule on the surface, the immobilized biomolecule forming the coating.

6. The method of claim 5, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

7. The method of claim 5, wherein the biomaterial comprises an amino acid residue.

8. The method of claim 5, wherein the amine forming agent is selected from the group consisting of bromine, bromide, bromite, hypobromite, chlorine, chloride, chlorite, hypochlorite, lead tetraacetate, benzyltrimethylammonium tribromide, [bis(trifluoroacetoxy)iodo]benzene, hydroxy (tosyloxy)iodobenzene and iodosylbenzene.

9. The method of claim 5, wherein the biomolecule is selected from the group consisting of an antithrombotic agent, an anti-inflammatory, an antibody, an antigen, an immunoglobulin, an enzyme, a hormone, a neurotransmitter, a cytokine, a protein, a globular protein, a cell attachment protein, a peptide, a cell attachment peptide, a proteoglycan, a toxin, an antibiotic agent, an antibacterial agent, an antimicrobial agent, a polysaccharide, a carbohydrate, a fatty acid, a drug, a vitamin, a DNA segment, a RNA segment, a nucleic acid, a lectin, a dye and a ligand.

10. The method of claim 5, wherein the biomolecule is a naturally occurring biomolecule.

11. The method of claim 5, wherein the biomolecule is a chemically synthesized biomolecule.

12. The method of claim 5, wherein the biomolecule is selected from the group consisting of a glycopeptide and a glycoprotein.

13. The method of claim 5, wherein at least a portion of the surface forms at least one of a tube, a rod, a membrane, a balloon, a bag and a sheet.

14. The method of claim 5, wherein the device comprises at least one of a biocompatible material selected from the group consisting of a metal, a titanium, a titanium alloy, a tin-nickel alloy, a shape memory alloy, an aluminum oxide, a platinum, a platinum alloy, a stainless steel, a MP35N stainless steel, a elgiloy, a stellite, a pyrolytic carbon, a silver carbon, a glassy carbon, a polymer, a polyamide, a polycarbonate, a polyether, a polyester, a polyolefin, a polyethylene, a polypropylene, a polystyrene, a polyurethane, a polyvinylchloride, a polyvinylpyrrolidone, a silicone elastomer, a fluoropolymer, a polyacrylate, a polyisoprene, a polytetrafluoroethylene, a rubber, a ceramic, a hydroxapatite, a human protein, a human tissue, an animal protein, an animal tissue, a bone, a skin, a tooth, a collagen, a laminin, a elastin, a fibrin, a wood, a cellulose, a compressed carbon and a glass.

15. A method of forming a coating on a surface of a medical device, the coating imparting improved biocompatibility characteristics to the surface, the method comprising the steps of:
  (a) providing the medical device, the device having a suitable biomaterial forming the surface, the biomaterial comprising an unsubstituted amide moiety;
  (b) combining the amide moiety with an amine forming agent to form an amine-functional surface;
  (c) providing a biomolecule, the biomolecule comprising a chemical moiety selected from the group consisting of an epoxide moiety and an isocyanate moiety; and
  (d) combining the chemical moiety with the surface to form a chemical bond, the chemical bond immobilizing the biomolecule on the surface, the immobilized biomolecule forming the coating.

16. The method of claim 15, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

17. The method of claim 15, wherein the biomaterial comprises an amino acid residue.

18. The method of claim 15, wherein the amine forming agent is selected from the group consisting of bromine, bromide, bromite, hypobromite, chlorine, chloride, chlorite, hypochlorite, lead tetraacetate, benzyltrimethylammonium tribromide, [bis(trifluoroacetoxy)iodo]benzene, hydroxy (tosyloxy)iodobenzene and iodosylbenzene.

19. The method of claim 15, wherein the biomolecule is selected from the group consisting of an antithrombotic agent, an anti-inflammatory, an antibody, an antigen, an immunoglobulin, an enzyme, a hormone, a neurotransmitter, a cytokine, a protein, a globular protein, a cell attachment protein, a peptide, a cell attachment peptide, a proteoglycan, a toxin, an antibiotic agent, an antibacterial agent, an antimicrobial agent, a polysaccharide, a carbohydrate, a fatty acid, a drug, a vitamin, a DNA segment, a RNA segment, a nucleic acid, a lectin, a dye and a ligand.

20. The method of claim 15, wherein the biomolecule is a naturally occurring biomolecule.

21. The method of claim 15, wherein the biomolecule is a chemically synthesized biomolecule.

22. The method of claim 15, wherein the biomolecule is selected from the group consisting of a glycopeptide and a glycoprotein.

23. The method of claim 15, wherein at least a portion of the surface forms at least one of a tube, a rod, a membrane, a balloon, a bag and a sheet.

24. The method of claim 15, wherein the device comprises at least one of a biocompatible material selected from the group consisting of a metal, a titanium, a titanium alloy, a tin-nickel alloy, a shape memory alloy, an aluminum oxide, a platinum, a platinum alloy, a stainless steel, a MP35N stainless steel, a elgiloy, a stellite, a pyrolytic carbon, a silver carbon, a glassy carbon, a polymer, a polyamide, a polycarbonate, a polyether, a polyester, a polyolefin, a polyethylene, a polypropylene, a polystyrene, a polyurethane, a polyvinylchloride, a polyvinylpyrrolidone, a silicone elastomer, a fluoropolymer, a polyacrylate, a polyisoprene, a polytetrafluoroethylene, a rubber, a ceramic, a hydroxapatite, a human protein, a human tissue, an animal protein, an animal tissue, a bone, a skin, a tooth, a collagen, a laminin, a elastin, a fibrin, a wood, a cellulose, a compressed carbon and a glass.

25. A method of forming a crosslinked coating on a surface of a medical device, the coating imparting improved biocompatibility characteristics to the surface, the method comprising the steps of:
  (a) providing the medical device, the device having a suitable biomaterial forming the surface, the biomaterial comprising unsubstituted amide moieties:
  (b) combining the amide moieties with an amine forming agent to form amine moieties;
  (c) providing biomolecules having at least one chemically reactive moiety selected from the group consisting of a 1,2-dihydroxy moiety and a 2-aminoalcohol moiety, combining periodate with the biomolecules to oxidize the chemically reactive moiety to form aldehyde moieties;
  (d) combining the biomolecules with the surface;
  (e) allowing the aldehyde moieties to combine with the amine moieties to form imine moieties; and
  (f) reacting the imine moieties with a reducing agent to form amine linkages, the amine linkages immobilizing and crosslinking the biomolecules on the surface, the immobilized and crosslinked biomolecules forming the coating.

26. The method of claim 25, wherein the periodate comprises at least one of periodic acid, sodium periodate, alkali metal periodates, and potassium periodate.

27. The method of claim 25, wherein the periodate is combined with the 2-aminoalcohol moieties in an aqueous solution having a pH between about 4 and about 9.

28. The method of claim 25, wherein the periodate is combined with the 2-aminoalcohol moieties in an aqueous solution having a temperature between about 0 and about 50 degrees Celsius.

29. The method of claim 25, wherein the oxidizing step is performed in the absence of light.

30. The method of claim 25, wherein the biomolecules and the surface are combined in an aqueous solution having a pH between about 6 and about 10.

31. The method of claim 25, wherein the biomolecules and the surface are combined in an aqueous solution having a temperature between about 0 and about 50 degrees Celsius.

32. The method of claim 25, wherein the reducing agent comprises at least one of sodium borohydride, sodium cyanoborohydride, and amine borane.

33. The method of claim 25, wherein the reducing agent is combined with the imine moieties in an aqueous solution having a pH between about 6 and about 10.

34. The method of claim 25, wherein the reducing agent is combined with the imine moieties in an aqueous solution having a temperature between about 0 and about 50 degrees Celsius.

35. A method of forming a coating on a surface of a medical device, the coating imparting improved biocompatibility characteristics to the surface, the method comprising the ordered steps of:
  (a) providing the medical device, the device having a suitable biomaterial forming the surface, the biomaterial comprising an unsubstituted amide moiety;
  (b) combining the amide moiety with an amine forming agent selected from the group consisting of bromine, bromide, bromite, hypobromite, chlorine, chloride, chlorite, hypochlorite, lead tetraacetate, benzyltrimethylammonium tribromide, [bis(trifluoroacetoxy)iodo]benzene, hydroxy(tosyloxy)iodobenzene and iodosylbenzene to form an amine-functional surface;
  (c) providing a biomolecule, the biomolecule comprising a 2-aminoalcohol moiety, combining a periodate comprising at least one of a periodic acid, a sodium periodate, an alkali metal periodate, and a potassium periodate, with the biomolecule in the absence of light and in an aqueous solution having a pH between about 4 and about 9 and a temperature between about 0 and about 50 degrees Celsius, the periodate oxidizing the 2-aminoalcohol moiety to form an aldehyde moiety;
  (d) combining the aldehyde moiety with the surface in an aqueous solution having a pH between about 6 and about 10 and a temperature between about 0 and about 50 degrees Celsius to form an imine moiety; and
  (e) reacting the imine moiety with at least one reducing agent selected from the group consisting of sodium borohydride, sodium cyanoborohydride and amine borane in an aqueous solution having a pH between about 6 and about 10 and a temperature between about 0 and about 50 degrees Celsius to form an amine linkage, the amine linkage immobilizing the biomolecule on the surface, the immobilized biomolecule forming the coating.

36. The method of claim 35, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

37. The method of claim 35, wherein the biomaterial comprises an amino acid residue.

38. The method of claim 35, wherein the biomolecule is selected from the group consisting of an antithrombotic agent, an anti-inflammatory, an antibody, an antigen, an immunoglobulin, an enzyme, a hormone, a neurotransmitter, a cytokine, a protein, a globular protein, a cell attachment protein, a peptide, a cell attachment peptide, a proteoglycan, a toxin, an antibiotic agent, an antibacterial agent, an antimicrobial agent, a polysaccharide, a carbohydrate, a fatty acid, a drug, a vitamin, a DNA segment, a RNA segment, a nucleic acid, a lectin, a dye and a ligand.

39. The method of claims 35, wherein the biomolecule is a naturally occurring biomolecule.

40. The method of claim 35, wherein the biomolecule is a chemically synthesized biomolecule.

41. The method of claim 35, wherein-the biomolecule comprises an amino acid residue.

42. The method of claim 41, wherein the amino acid residue is selected from the group consisting of a N-terminal serine, a N-terminal threonine and a 5-hydroxylysine.

43. The method of claim 35, wherein at least a portion of the surface forms at least one of a tube, a rod, a membrane, a balloon, a bag and a sheet.

44. The method of claim 35, wherein the device comprises at least one of a biocompatible material selected from the group consisting of a metal, a titanium, a titanium alloy, a tin-nickel alloy, a shape memory alloy, an aluminum oxide, a platinum, a platinum alloy, a stainless steel, a MP35N stainless steel, a elgiloy, a stellite, a pyrolytic carbon, a silver carbon, a glassy carbon, a polymer, a polyamide, a polycarbonate, a polyether, a polyester, a polyolefin, a polyethylene, a polypropylene, a polystyrene, a polyurethane, a polyvinylchloride, a polyvinylpyrrolidone, a silicone elastomer, a fluoropolymer, a polyacrylate, a polyisoprene, a polytetrafluoroethylene, a rubber, a-ceramic, a hydroxapatite, a human protein, a human tissue, an animal protein, an animal tissue, a bone, a skin, a tooth, a collagen, a laminin, a elastin, a fibrin, a wood, a cellulose, a compressed carbon and a glass.

45. A method of forming a coating on a surface of a medical device, the coating imparting improved biocompatibility characteristics to the surface, the method comprising the ordered steps of:
    (a) providing the medical device, the device having a suitable biomaterial forming the surface, the biomaterial comprising an unsubstituted amide moiety;
    (b) combining the amide moiety with an amine forming agent selected from the group consisting of bromine, bromide, bromite, hypobromite, chlorine, chloride, chlorite, hypochlorite, lead tetraacetate, benzyltrimethylammonium tribromide, [bis(trifluoroacetoxy)iodo]benzene, hydroxy(tosyloxy)iodobenzene and iodosylbenzene to form an amine-functional surface;
    (c) providing a biomolecule, the biomolecule comprising a 1,2-dihydroxy moiety, combining a periodate comprising at least one of a periodic acid, a sodium periodate, an alkali metal periodate, and a potassium periodate, with the biomolecule in the absence of light and in an aqueous solution having a pH between about 4 and about 9 and a temperature between about 0 and about 50 degrees Celsius, the periodate oxidizing the 1,2-dihydroxy moiety to form an aldehyde moiety;
    (d) combining the aldehyde moiety with the surface in an aqueous solution having a pH between about 6 and about 10 and a temperature between about 0 and about 50 degrees Celsius to form an imine moiety; and
    (e) reacting the imine moiety with at least one reducing agent selected from the group consisting of sodium borohydride, sodium cyanoborohydride and amine borane in an aqueous solution having a pH between about 6 and about 10 and a temperature between about 0 and about 50 degrees Celsius to form an amine linkage, the amine linkage immobilizing the biomolecule on the surface, the immobilized biomolecule forming the coating.

46. The method of claim 45, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

47. The method of claim 45, wherein the biomaterial comprises an amino acid residue.

48. The method of claim 45, wherein the biomolecule is selected from the group consisting of an antithrombotic agent, an anti-inflammatory, an antibody, an antigen, an immunoglobulin, an enzyme, a hormone, a neurotransmitter, a cytokine, a protein, a globular protein, a cell attachment protein, a peptide, a cell attachment peptide, a proteoglycan, a toxin, an antibiotic agent, an antibacterial agent, an antimicrobial agent, a polysaccharide, a carbohydrate, a fatty acid, a drug, a vitamin, a DNA segment, a RNA segment, a nucleic acid, a lectin, a dye and a ligand.

49. The method of claim 45, wherein the biomolecule is a naturally occurring biomolecule.

50. The method of claim 45, wherein the biomolecule is a chemically synthesized biomolecule.

51. The method of claim 45, wherein the biomolecule is selected from the group consisting of a glycopeptide and a glycoprotein.

52. The method of claim 45, wherein at least a portion of the surface forms at least one of a tube, a rod, a membrane, a balloon, a bag and a sheet.

53. The method of claim 45, wherein the device comprises at least one of a biocompatible material selected from the group consisting of a metal, a titanium, a titanium alloy, a tin-nickel alloy, a shape memory alloy, an aluminum oxide, a platinum, a platinum alloy, a stainless steel, a MP35N stainless steel, a elgiloy, a stellite, a pyrolytic carbon, a silver carbon, a glassy carbon, a polymer, a polyamide, a polycarbonate, a polyether, a polyester, a polyolefin, a polyethylene, a polypropylene, a polystyrene, a polyurethane, a polyvinylchloride, a polyvinylpyrrolidone, a silicone elastomer, a fluoropolymer, a polyacrylate, a polyisoprene, a polytetrafluoroethylene, a rubber, a ceramic, a hydroxapatite, a human protein, a human tissue, an animal protein, an animal tissue, a bone, a skin, a tooth, a collagen, a laminin, a elastin, a fibrin, a wood, a cellulose, a compressed carbon and a glass.

* * * * *